(12) United States Patent
Shai et al.

(10) Patent No.: US 7,693,565 B2
(45) Date of Patent: Apr. 6, 2010

(54) METHOD AND APPARATUS FOR AUTOMATICALLY POSITIONING A STRUCTURE WITHIN A FIELD OF VIEW

(75) Inventors: Eyal Shai, Karkur (IL); Yaron Hefetz, Herzeliya (IL); Deborah Ruth Zelnik, Haifa (IL)

(73) Assignee: General Electric Company, Schenectady, NY (US)

( * ) Notice: Subject to any disclaimer, the term of this patent is extended or adjusted under 35 U.S.C. 154(b) by 422 days.

(21) Appl. No.: 11/395,634

(22) Filed: Mar. 31, 2006

(65) Prior Publication Data

US 2007/0232881 A1    Oct. 4, 2007

(51) Int. Cl.
*A61B 5/05* (2006.01)
*A61B 6/00* (2006.01)

(52) U.S. Cl. .................. 600/407; 600/425; 600/436; 378/4

(58) Field of Classification Search .......... 600/407, 600/410; 378/4, 62
See application file for complete search history.

(56) References Cited

U.S. PATENT DOCUMENTS

| | | | |
|---|---|---|---|
| 5,608,221 A * | 3/1997 | Bertelsen et al. ....... 250/363.03 |
| 5,906,578 A * | 5/1999 | Rajan et al. .................. 600/424 |
| 6,429,434 B1 * | 8/2002 | Watson et al. .......... 250/363.04 |
| 6,764,217 B2 * | 7/2004 | Yasuda et al. ................ 378/205 |
| 6,774,358 B2 * | 8/2004 | Hamill et al. ............. 250/252.1 |
| 6,956,925 B1 | 10/2005 | Hoffman |
| 2004/0015072 A1 * | 1/2004 | Pelletier et al. ............. 600/410 |
| 2005/0129295 A1 | 6/2005 | Shanmugam et al. |
| 2006/0116567 A1 * | 6/2006 | Nilsen et al. ................. 600/407 |
| 2006/0140339 A1 * | 6/2006 | Marcovitch .................. 378/20 |
| 2006/0237652 A1 * | 10/2006 | Kimchy et al. ......... 250/363.02 |

\* cited by examiner

*Primary Examiner*—Eric F Winakur
*Assistant Examiner*—Michael T Rozanski
(74) *Attorney, Agent, or Firm*—Dean Small; Small Patent Law Group

(57) ABSTRACT

A medical imaging system for automatically positioning a structure of interest within a field of view (FOV) of an imaging detector comprises at least one imaging detector for detecting radiation. The imaging detector has a FOV and detects a first image while at a first system position with respect to a predetermined reference point. A structure detecting module detects a structure of interest within the first image and determines whether the structure of interest is within the FOV of the imaging detector. The structure detecting module determines a second system position with respect to the predetermined reference point at which the structure of interest will be positioned within the FOV of the imaging detector, and a controller moves the FOV of the imaging detector to the second system position.

23 Claims, 5 Drawing Sheets

METHOD AND APPARATUS FOR AUTOMATICALLY POSITIONING A STRUCTURE WITHIN A FIELD OF VIEW

BACKGROUND OF THE INVENTION

This invention relates generally to imaging devices, and more particularly, to automatically positioning a structure within the field of view of the imaging device The medical imaging industry has developed many different types of imaging systems that are useful for diagnostic purposes. Some systems image using a single modality, such as computerized tomography (CT), positron emission tomography (PET), and nuclear medicine (NM). Other systems offer a combination of imaging systems, such as CT-PET and CT-NM, and may be referred to as multi-modality systems. The multi-modality systems may acquire images using one modality or acquire images in more than one mode simultaneously.

When imaging a specific structure, organ or anatomy of a patient, such as the heart, liver or kidney, the patient must be positioned in relation to the detector or camera of the imaging system such that the structure to be imaged is within the field of view (FOV) of one or more imaging detectors. Certain scanning methods, such as nuclear tomography cardiology scanning, wherein the detector(s) rotate around the patient, require patient positioning so that the heart is as close as possible to the center of the detector's FOV. If the patient is not positioned correctly, the scan must be stopped and the patient repositioned. In other cases, the positioning problem may not be apparent during the acquisition, and thus acquired data may be reviewed and/or processed before it is found to be deficient.

Within NM, the patient is typically positioned by an operator who manually adjusts the patient table and the imaging detector(s) while viewing the persistence image until the operator determines that the patient's heart or other structure of interest is centered within the FOV of the detector(s). This may be cumbersome and time consuming depending upon the location of the monitor displaying the persistence image, as well as adding to the discomfort of the patient who needs to lie still on the patient table during the positioning. Manually positioning the patient becomes increasingly complex with PET systems, as well as with an NM camera having a multipinhole collimator or when the NM camera FOV is small, such as in dedicated cardiology systems.

Therefore, a need exists for automatically positioning a patient within the FOV of the imaging detector(s) of a medical imaging system. Certain embodiments of the present invention are intended to meet these needs and other objectives that will become apparent from the description and drawings set forth below.

BRIEF DESCRIPTION OF THE INVENTION

In one embodiment, a medical imaging system for automatically positioning a structure of interest within a field of view (FOV) of an imaging detector comprises at least one imaging detector for detecting radiation. The imaging detector has a FOV and detects a first image while at a first system position with respect to a predetermined reference point. A structure detecting module detects a structure of interest within the first image and determines whether the structure of interest is within the FOV of the imaging detector. The structure detecting module determines a second system position with respect to the predetermined reference point at which the structure of interest will be positioned within the FOV of the imaging detector, and a controller moves the FOV of the imaging detector to the second system position.

In another embodiment, a method for automatically positioning a structure of interest within a field of view (FOV) of an imaging detector comprises detecting a first image comprising a structure of interest with an imaging detector. The imaging detector has a FOV and is located at a first system position with respect to a predetermined reference point. The FOV of the imaging detector is automatically positioned at a second system position which is different from the first system position. A second image is detected with the imaging detector at the second system position. The first and second images are compared to identify a corresponding system position at which more of the structure of interest is positioned within the FOV.

Figure 1:
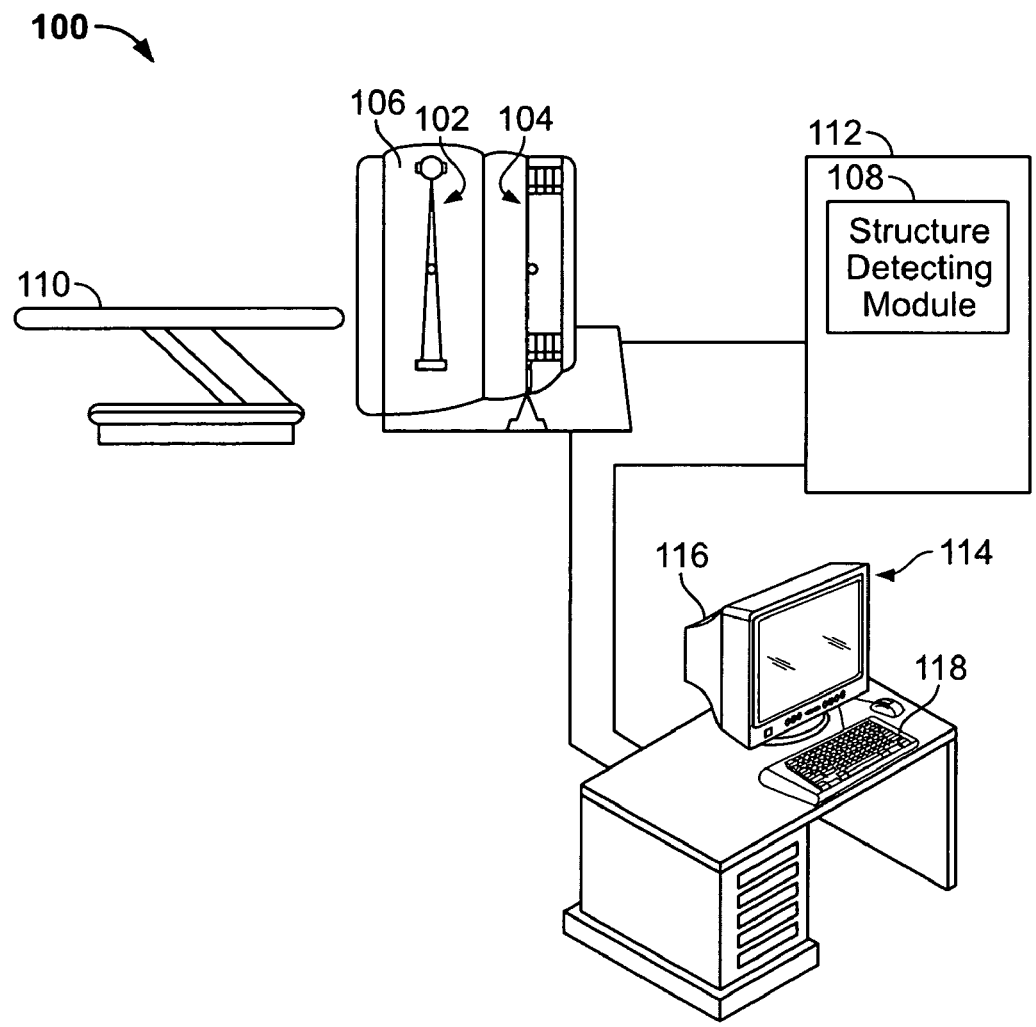
FIG. 1 illustrates a multi-modality imaging system which has a CT and a PET system formed in accordance with an embodiment of the present invention.

The foregoing summary, as well as the following detailed description of certain embodiments of the present invention, will be better understood when read in conjunction with the appended drawings. The figures illustrate diagrams of the functional blocks of various embodiments. The functional blocks are not necessarily indicative of the division between hardware circuitry. Thus, for example, one or more of the functional blocks (e.g., processors or memories) may be implemented in a single piece of hardware (e.g., a general purpose signal processor or a block or random access memory, hard disk, or the like). Similarly, the programs may be stand alone programs, may be incorporated as subroutines in an operating system, may be functions in an installed imaging software package, and the like. It should be understood that the various embodiments are not limited to the arrangements and instrumentality shown in the drawings.

DETAILED DESCRIPTION OF THE INVENTION

FIG. 1 illustrates a multi-modality imaging system 100 which has a CT system 102 and a PET system 104 mounted around a bore in a housing 106. The system 100 also includes a patient table 110, a processing unit 112 with a structure detecting module 108, and a control station 114. The processing unit 112 also includes one or more processors, one or more memories, and associated electronics for processing image data acquired by the CT system 102 and the PET system 104. A patient table controller (not shown) moves the patient table 110 up and down and into the bore in response to commands received from the control station 114. The control station 114 typically includes a display 116 and one or more input devices 118 such as a keyboard or a mouse. The operator uses the input devices 118 to control the operation of the system 100 and process and display images on the display 116.

When imaging a particular structure within a patient with the PET system 104, the entire structure of interest is positioned within the field of view (FOV) of the PET system 104. Any portion of the structure which is outside the FOV will be truncated and the study may have to be reacquired. Co-registration of the CT and PET images is maintained by the use of the same patient table 110, thus creating a common predetermined reference point for the CT and PET systems 102 and 104.

Optionally, persistence images detected by the PET system 104 may be used to position the structure of interest within the FOV of the PET system 104 based on count rate. A radiopharmaceutical has been administered to the patient and accumulates in the structure of interest. The patient table 110 may be automatically moved into the bore of the housing 106 while the processing unit 112 monitors the count rate of photons detected by the PET detectors (not shown). The patient is properly positioned when the highest count rate is detected.

Figure 2:
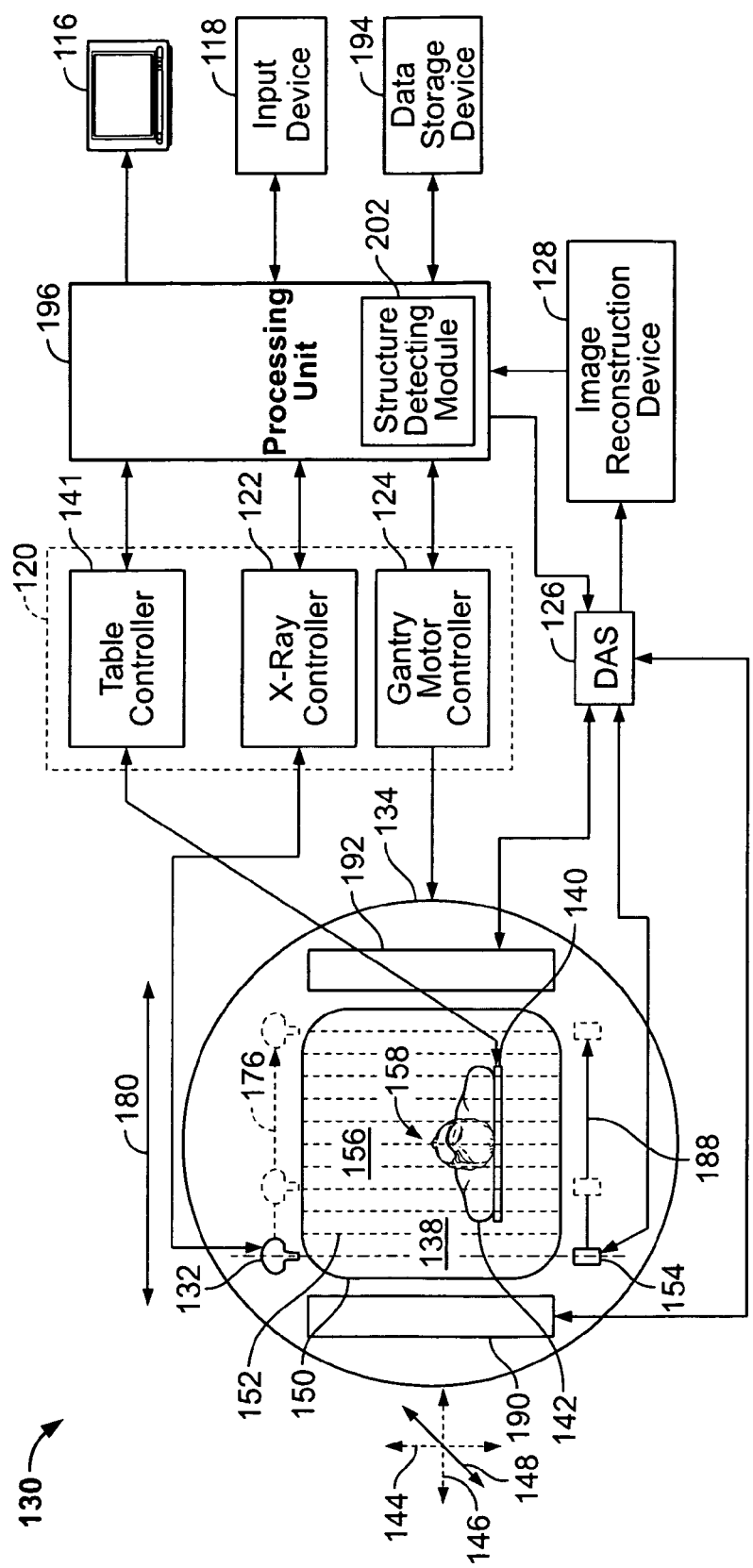
FIG. 2 is a schematic illustration of a CT-NM multi-modality imaging system formed in accordance with an embodiment of the present invention.

FIG. 2 is a schematic illustration of a CT-NM multi-modality imaging system 130. An x-ray source 132 is mounted on a gantry 134 which may having an aperture 138 therethrough. Alternatively, the gantry 134 may be fabricated from a plurality of gantry segments, each of which may be separated from an adjacent segment by a space. A patient table 140 is configured with a support mechanism (not shown) to support and carry a patient 142 in a plurality of viewing positions within the aperture 138. A table controller 141 may automatically command the patient table 140 to move in any of at least two substantially orthogonal directions, including, for example, an up-down direction 144, an in-out direction 148 and optionally a right-left direction 146. The table controller 141 may move the patient table 140 to properly align the structure of interest within the FOV of one or more imaging detectors prior to a diagnostic scan of the patient 142. Also, the patient table 140 may be manually controlled by an operator who physically moves the patient table 140 or uses button or switches to direct movement. For example, the operator may move the patient table 140 to an initial position which is believed to roughly place the structure of interest within the FOV.

In the non-limiting exemplary embodiment, the x-ray source 132 generates and transmits a pencil-beam of x-rays 150 to an x-ray detector 154 from a first side of the gantry 134 to a second opposite side of the gantry 134 along a detector-source axis 152. The x-ray detector 154 may comprise a single detector and the x-ray source 132 a single x-ray source. The x-ray source 132 and x-ray detector 154 are mounted to the gantry 134 and controlled to move in cooperation through translation mechanisms 176 and 188, respectively, in a laterally translational direction 180. Thus, the pencil-beam of x-rays 150 may be directed to the x-ray detector 154 which maintains a relative position with respect to the x-ray source 132 during a scan.

Alternatively, the x-ray source 132 may be positioned in a central position along the laterally translational direction 180 and be configured to produce a sweeping pencil-beam of a flood of x-ray. A linear x-ray detector (not shown) would be positioned opposite the x-ray source 132 and replace the small x-ray detector 154. Alternatively, an x-ray source producing a fan-like x-ray beam may be used in conjunction with an array of x-ray detectors. Alternatively, an x-ray source producing a cone-beam may be used with a two dimensional x-ray detector.

First and second gamma cameras 190 and 192 are mounted to the gantry 134 to detect gamma rays emitted from a radiopharmaceutical within the patient 142. In FIG. 2, the second gamma camera 192 is mounted on the gantry 134 opposite the first gamma camera 190 such that the first and second gamma cameras 190 and 192 may also be used to detect coincident emissions of gammas, for example, for use in PET imaging. Optionally, a single gamma camera 190 may be used. Optionally, one or both of the first and second gamma cameras 190 and 192 may be configured to alternatively or simultaneously acquire x-ray data, such as a CZT detector or other multi-modality detector known in the art. Therefore, the x-ray detector 154 may not be needed. Instead, the x-ray source 132 may be positioned opposite to one of the first or second gamma cameras 190 and 192.

A controller unit 120 controls the movement and operation of x-ray source 132, x-ray detector 154, first and second gamma cameras 190 and 192, and the patient table 140. The controller unit 120 may have an x-ray controller 122, a gantry motor controller 124, and the table controller 141. The table controller 141 may control the patient table 140 automatically to position the patient 142 relative to the FOV of the first and/or second gamma cameras 190 and 192. The x-ray controller 122 may provide power and timing signals to the x-ray source 132, while the gantry motor controller 124 may control the position of the first and second gamma cameras 190 and 192, as well as translational speed and angular position of the x-ray source 132 and x-ray detector 154.

A data acquisition system (DAS) 126 receives the electrical signal data produced by the x-ray detector 154 and the first and second gamma cameras 190 and 192 and converts this data into digital signals for subsequent processing. An image reconstruction device 128, a data storage device 194 and a processing unit 196 may also be provided.

The NM and CT functions may be used together or separate from each other. Optionally, the first and second gamma cameras 190 and 192 may be mounted on a second gantry (not shown) that is axially spaced from the gantry 134 to allow the first and second gamma cameras 190 and 192 separate rotational movement. Accordingly, the gantry 134, the second gantry and the patient table 140 are controlled to ensure co-registration of image data acquired using the NM and CT functions.

A system position may be defined by the processing unit 196 to identify the positions of all components and their relation to each other with respect to a predetermined reference point. The components may be any fixed or moving structure with the system 130, such as the patient table 140, first and second gamma cameras 190 and 192, position of the x-ray source 132 and detector 154, and the like, each of which references the predetermined reference point, such as a zero position or an initial reference position.

Optionally, the first and second gamma cameras 190 and 192 may be operated in persistence mode. The table controller 141 moves the patient table 140 while the DAS 126 and/or processing unit 196 detect a count rate from each of the first and second gamma cameras 190 and 192. For example, the patient 142 may be positioned on the patient table 140 to be equidistant between the first and second gamma cameras 190 and 192. The table controller 141 may first move the patient table along the in-out direction 148 to determine a horizontal table position having a maximum count rate. The table controller 141 may then move the patient table 140 along the up-down direction 144 to determine a vertical table position having a maximum count rate.

Figure 3:
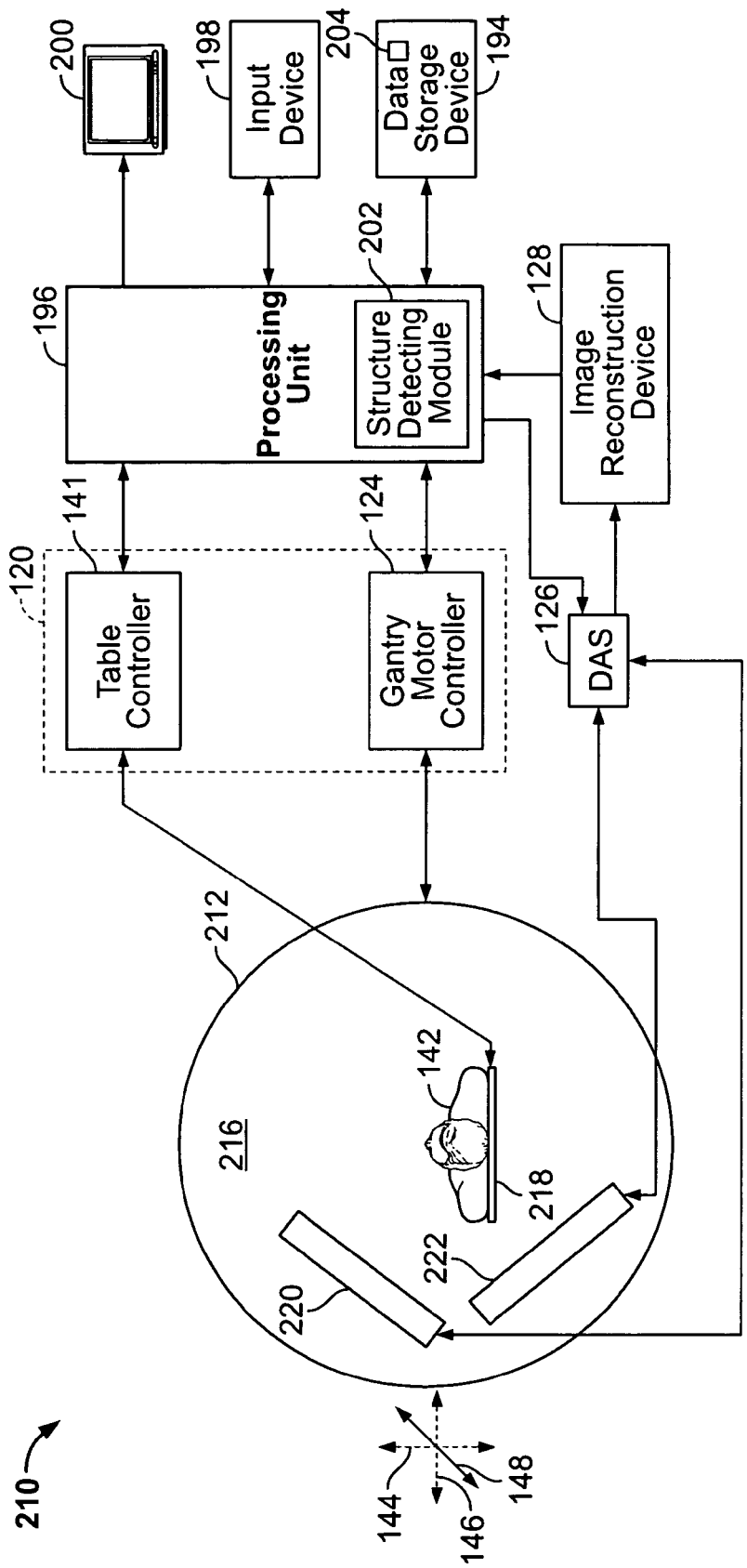
FIG. 3 is a schematic illustration of an NM imaging system formed in accordance with an embodiment of the present invention.

FIG. 3 is a schematic illustration of an NM imaging system 210. First and second gamma cameras 220 and 222 are mounted on a gantry 212 with an aperture 216 there-through. Alternatively, the gantry 212 may comprise a plurality of gantry segments which may be separated from one another. Although two gamma cameras are illustrated, it should be understood that one, two, three, or more than three gamma cameras may be used.

A patient table 218 is configured with a support mechanism (not shown) to support and carry the patient 142 in a plurality of viewing positions within the aperture 216. The patient table 218 may be manually controlled by an operator as discussed previously or automatically by the table controller 141 to move the patient table 218 in any of at least two substantially orthogonal directions, such as the up-down direction 144 and the in-out direction 148, and optionally in the right-left direction 146.

The gantry motor controller 124 may rotate the first and second gamma cameras 220 and 222 around, towards, and away from the patient 142. The gantry motor controller 124 may be automatically commanded by the processing unit 196, as well as manually controlled by the operator.

To position the structure of interest within the FOV of the first and second gamma cameras 220 and 222, a planar image or a planar persistence image may be used to locate the structure of interest. In one embodiment, the patient is slowly moved into the aperture 216 of the gantry 212 while an image is formed. The structure detecting module 202 may identify the desired structure of interest and stop the motion of the patient table 218 automatically when the structure of interest is fully within the FOV or at the center of the FOV. Anti-collision software and/or sensors (not shown) may also be used to ensure that the patient 142 does not collide with the first and second gamma cameras 220 and 222.

The optimal imaging position identified specifically for the patient 142 may also be referred to as a patient system position 204. The patient system position 204 comprises data identifying the unique, optimal positions for imaging the patient 142, such as identifying the specific position of the patient table 218 and first and second gamma cameras 220 and 222. For other systems, such as the multi-modality systems 100 and 130 of FIGS. 1 and 2, additional data may be stored.

By way of example, multiple cardiac scans may be acquired of the patient 142. The first scan is a non-stress scan and a second scan is a stressed scan. The processing unit 196 may store the patient system position 204 in the data storage device 194 when the first scan is acquired. The patient 142 leaves the patient table 218 between the first and second scans. When the patient 142 returns for the second scan, the patient system position 204 for the patient 142 is retrieved and the appropriate system components moved to their identified optimal positions with respect to the predetermined reference point, which automatically positions the anatomy of interest, in this example the heart, within the FOV of the first and second detectors 220 and 222 for the second scan. Optionally, first and second scan may be of the same type taken at different times even on different days.

Figure 4:
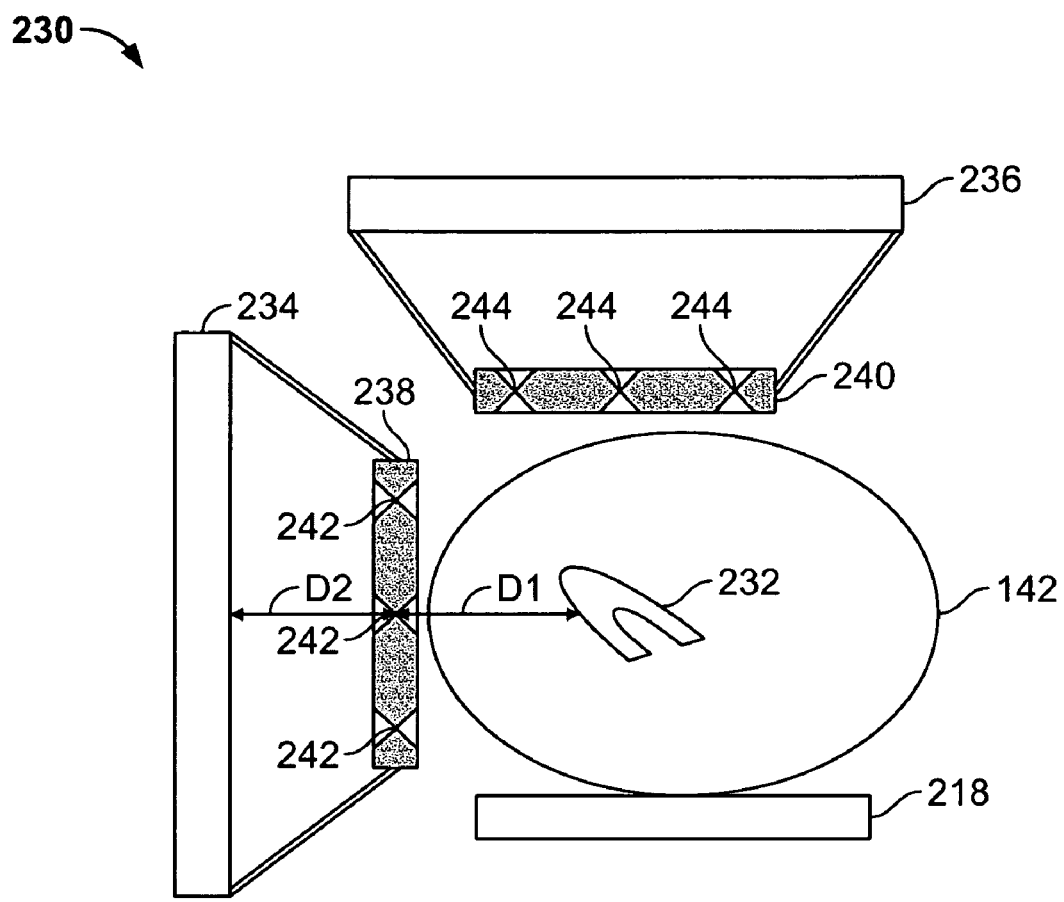
FIG. 4 illustrates a multiple-pinhole NM camera which may be used to automatically position a structure of interest within a field of view formed in accordance with an embodiment of the present invention.

FIG. 4 illustrates a multiple-pinhole NM camera 230 which may be used to automatically position the patient 142 prior to acquiring a scan of a structure of interest 232. For example, first and second gamma cameras 234 and 236 may be used with the patient table 218, controllers, processing components, and structure detecting module 202 of FIG. 3. The first and second gamma cameras 234 and 236 may used with sensors (not shown) to detect a surface of the patient 142 to avoid collision. The first and second gamma cameras 234 and 236 are fitted with first and second pinhole collimators 238 and 240. An inverted image of the structure of interest 232 is formed on each of the first and second gamma cameras 234 and 236 for each pinhole 242 and 244. Therefore, the structure of interest 232 is imaged from multiple directions.

The processing unit 196 may acquire a planar image with each of the first and second gamma cameras 234 and 236. The structure detecting module 202 analyzes the images formed by each pinhole 242 and 244 within the planar images to determine an optimal system position. The patient table 218 may then be moved to position the patient optimally to center the structure of interest 232 with respect to each of the pinholes 242 and 244. Optionally, the first and second gamma cameras 234 and 236 may be moved with respect to the patient 142 and patient table 218, and/or the position of the pinholes 242 and 244 may be moved. The processing unit 196 may also analyze the images to determine if the configuration should be changed, such as by changing the magnification factor determined by structure to pinhole distance D1 and pinhole to detector distance D2.

Alternatively, the patient 142 may be initially positioned a distance away from the first and second gamma cameras 234 and 236 which is greater than the distance used for diagnostic scanning. The structure detecting module 202, processing unit 196, table controller 141 and gantry motor controller 124 may then go through an iterative process of detecting the location of the structure of interest 232 and moving the patient table 218, first and/or second gamma cameras 234 and 236, first and/or second pinhole collimators 238 and 240, and/or pinholes 242 and 244 until optimum positioning of the structure 232 is achieved.

Optionally, if the first and second gamma cameras 234 and 236 are constructed in segments which are configurable, such that each pinhole 242 and 244 relates to a separate segment, the segments may be moved relative to the patient 142 until optimum positioning of the structure 232 is achieved.

Figure 5:
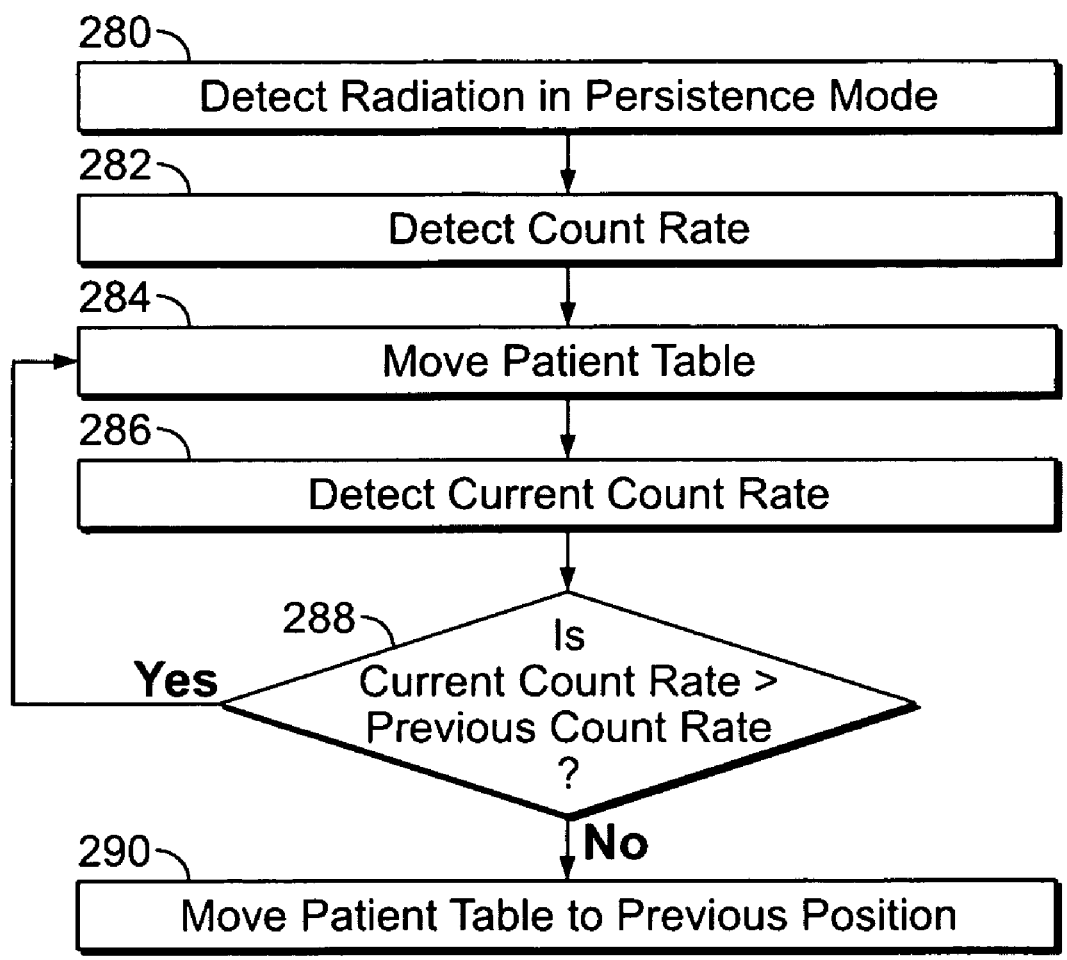
FIG. 5 illustrates a flow chart of a method to position a structure of interest within a FOV based on count rate detected from persistence images in accordance with an embodiment of the present invention.

FIG. 5 illustrates a flow chart of a method to position a structure of interest within a FOV based on count rate detected from persistence images. The method will be discussed with relation to FIG. 3, but other imaging systems may be used. In step 280, the first and second gamma cameras 220 and 222 detect radiation in persistence mode, such as gamma rays from the patient 142. Coincidence detection may be used if the first and second gamma cameras 220 and 222 are acquiring PET data. In step 282, the processing unit 196 detects the count rate for each of the first and second gamma cameras 220 and 222.

In step 284, the table controller 141 moves the patient table 218, such as into the aperture 216 of the gantry 212 in the in-out direction 148. In step 286, the processing unit 196 detects the current count rate for each of the first and second gamma cameras 220 and 222. In step 288, the processing unit 196 determines if the current count rate is greater than the previous count rate of step 282. If yes, flow returns to step 284 where the patient table 218 is moved in the same direction as the previous table move. In step 286, the current count rate is determined, and in step 288, the current count rate is compared to the previous count rate. As long as the current count rate increases relative to the previous count rate, the table controller 141 continues to move patient table 218 in the same direction.

If, in step 288, the current count rate is less than the previous count rate, the method passes to step 290 where the table controller 141 moves the patient table 218 to the previous position which coincides with the position of highest count rate. Alternatively, the method of FIG. 5 may be repeated for the vertical direction, moving the patient table 218 in the up-down direction 144.

The method of FIG. 5 may also be applied to find an average optimal patient position for a multi-segment imaging system, such as the multiple-pinhole NM camera 230 of FIG. 4 or the imaging system 130 which may be formed of movable segments as previously discussed. The optimal position for each segment or pinhole 242 and 244 may be detected separately or concurrently.

First, the segments are positioned at nominal positions or a first system position and the count rate is detected (step 282). In step 284, instead of moving the patient table 218, one, multiple or all of the segments or pinholes 244 and 246 are moved, which moves the corresponding FOV. In step 286, the current count rate is detected, and in step 288, the previous count rates are compared to the current count rates. The segments or pinholes 244 and 246 are moved again in step 284. The comparing of previous and current count rates along with moving the FOV(s) is iterative, until the processing unit 196 has determined that the average optimal patient position has been achieved.

While the invention has been described in terms of various specific embodiments, those skilled in the art will recognize that the invention can be practiced with modification within the spirit and scope of the claims.

What is claimed is:

1. A medical imaging system for automatically positioning a structure of interest within a field of view of an imaging detector, comprising:
    at least one imaging detector for detecting radiation, the imaging detector having a field of view (FOV), the imaging detector configured to detect a first image while at a first system position with respect to a predetermined reference point and to detect a second image at a second system position;
    a structure detecting module configured to automatically detect a structure of interest based on a count rate associated with the first image, the structure detecting module further configured to determine whether at least a portion of the structure of interest is within the FOV and to automatically determine a corresponding system position with respect to the predetermined reference point at which more of the structure of interest will be positioned within the FOV of the imaging detector at the corresponding system position based on the count rates associated with the first and second images; and
    a controller configured to move the FOV of the imaging detector to the corresponding system position.

2. The medical imaging system of claim 1, further comprising a patient table, wherein the first and second system positions further comprise first and second table positions, the controller further configured to move the patient table to the second table position.

3. The medical imaging system of claim 1, further comprising a gantry, a patient table, and a multi-pinhole collimator, the controller further configured to move at least one of the gantry, the patient table, the multi-pinhole collimator and the at least one imaging detector to the corresponding system position.

4. The medical imaging system of claim 1, further comprising a patient table, wherein the first system position further comprises at least one of a first longitudinal patient table position and a first vertical patient table position, and wherein the corresponding system position further comprises at least one of a second longitudinal patient table position and a second vertical patient table position.

5. The medical imaging system of claim 1, further comprising a memory configured to store the corresponding system position, the controller further configured to retrieve the corresponding system position from the memory and automatically position the FOV of the imaging detector based on the corresponding system position before acquiring at least one subsequent image.

6. The medical imaging system of claim 1, wherein the first image further comprises a persistence image.

7. The medical imaging system of claim 1, wherein the at least one imaging detector further comprises at least first and second gamma cameras.

8. The medical imaging system of claim 1, wherein the at least one imaging detector is configured to acquire at least one of gamma rays and x-rays.

9. The medical imaging system of claim 1, wherein the structure detecting module is further configured to determine a maximum count rate based on the first and second images and move a patient table horizontally to the corresponding system position based on the maximum count rate.

10. The medical imaging system of claim 1, wherein the structure detecting module is further configured to determine a maximum count rate based on the first and second images and move a patient table vertically to the corresponding system position based on the maximum count rate.

11. The medical imaging system of claim 1, wherein the controller is further configured to automatically stop a movement of a patient table when the structure of interest is fully within the field of view.

12. The medical imaging system of claim 1, wherein the structure detecting module is further configured to:
    determine when the structure of interest is within a predetermined distance of the at least one imaging detector; and
    automatically stop a movement of a patient table when the structure of interest is within the predetermined distance.

13. The medical imaging system of claim 1, further comprising a multi-pinhole collimator, the controller is further configured to modify an imaging position of the at least one imaging detector based on at least one of a distance between the at least one imaging detector and the pinhole collimator and a distance between the collimator and the structure of interest.

14. A medical imaging system for automatically positioning a structure of interest within a field of view of an imaging detector, comprising:
    at least one imaging detector for detecting radiation, the imaging detector having a field of view (FOV), the imaging detector configured to detect a first image while at a first system position with respect to a predetermined reference point and to detect a second image at a second system position;
    a structure detecting module configured to automatically detect a structure of interest based on a count rate associated with the first image, the structure detecting module further configured to determine whether at least a portion of the structure of interest is within the FOV and to automatically determine whether more of the structure of interest is within the FOV at the second system position based on a count rate associated with the second image and to automatically determine a third system position at which the structure of interest will be positioned closer to a center of the FOV; and
    a controller configured to move the FOV of the imaging detector to the third system position.

15. A method for automatically positioning a structure of interest within a field of view of an imaging detector, comprising:

detecting a first image with an imaging detector, the first image comprising a structure of interest within a patient, the imaging detector having a field of view (FOV), the imaging detector being located at a first system position with respect to a predetermined reference point;

automatically positioning the FOV of the imaging detector at a second system position with a controller, the first and second system positions being different from one another;

detecting a second image with the imaging detector at the second system position; and comparing the first and second images with a structure detecting module to identify a corresponding system position at which more of the structure of interest is positioned within the FOV, wherein the first and second images further comprise persistence images, wherein the first and second images have first and second count rates, respectively, wherein the comparing step further comprises identifying a higher count rate between the first and second count rates.

16. The method of claim 15, wherein the second system position identifies a position of a patient table configured to support the patient, the automatically positioning step further comprising moving the patient table relative to the FOV of the imaging detector to locate the patient table at the second system position.

17. The method of claim 15, wherein the second system position identifies a position of the imaging detector, the automatically positioning step further comprising moving the imaging detector relative to the patient to locate the imaging detector at the second position.

18. The method of claim 15, further comprising:
storing a patient system position in a memory, the patient system position being based on the corresponding system position, the patient system position being associated with the patient; and
retrieving the patient system position from the memory to locate the FOV of the imaging detector and the structure of interest within the patient relative to one another before acquiring at least one subsequent image.

19. The method of claim 15, further comprising
automatically positioning at least one of the patient and the imaging detector at a third position with the controller, the second and third positions being different from one another;

detecting a third image with the imaging detector at the third position; and comparing the second and third images with the structure detecting module to identify the corresponding system position at which more of the structure of interest is positioned within the FOV.

20. The method of claim 15, the comparing step identifying the corresponding system position based on the structure of interest being positioned closer to a center of the FOV.

21. The method of claim 15, wherein the imaging detector is configured to detect at least one of gamma rays and x-rays.

22. The method of claim 15, wherein the automatically positioning further comprises iteratively positioning at least two pinholes within a multi-pinhole collimator at different positions with respect to each other, and wherein the comparing further comprises comparing images detected at the different positions to identify an average optimal system position based on count rates associated with each of the images.

23. A method for automatically positioning a structure of interest within a field of view of an imaging detector, comprising:
detecting a first image with an imaging detector, the first image comprising a structure of interest within a patient, the imaging detector having a field of view (FOV), the imaging detector being located at a first system position with respect to a predetermined reference point;
automatically positioning the FOV of the imaging detector at a second system position with a controller, the first and second system positions being different from one another;
detecting a second image with the imaging detector at the second system position; and
comparing the first and second images with a structure detecting module to identify a corresponding system position at which more of the structure of interest is positioned within the FOV, wherein the automatically positioning further comprises iteratively positioning at least one of the imaging detector, a patient table, and a multi-pinhole collimator at different positions with respect to each other, and wherein the comparing further comprises comparing images detected at the different positions to identify a system position that corresponds to a highest count rate.

* * * * *